United States Patent [19]
Sato et al.

[11] 4,348,903
[45] Sep. 14, 1982

[54] ELECTROMAGNETIC ULTRASONIC APPARATUS

[75] Inventors: Ichiya Sato, Hitachi; Kazuo Miyagawa; Yukito Sasaki, both of Kisarazu; Koji Kawamura; Shuichi Sato, both of Kimitsu; Soji Sasaki, Hitachi; Jun Kubota, Hitachi; Susumu Itoh, Hitachi, all of Japan

[73] Assignees: Nippon Steel Corporation; Hitachi, Ltd., both of Tokyo, Japan

[21] Appl. No.: 180,043

[22] Filed: Aug. 21, 1980

[30] Foreign Application Priority Data

Aug. 24, 1979 [JP] Japan .............................. 54-107190

[51] Int. Cl.³ ............................................ G01N 29/00
[52] U.S. Cl. ........................................................ 73/643
[58] Field of Search ................. 73/643, 618; 324/222

[56] References Cited

U.S. PATENT DOCUMENTS

4,164,873  8/1979  Böttcher et al. ....................... 73/643

FOREIGN PATENT DOCUMENTS

52-86388  7/1977  Japan ..................................... 73/643

270317  8/1970  U.S.S.R. .................................. 73/643

OTHER PUBLICATIONS

G. J. Parkinson et al., "Non-Contact Ultrasonics", *British Journal of NDT*, pp. 178–184, Jul. 1977.

*Primary Examiner*—Stephen A. Kreitman
*Attorney, Agent, or Firm*—Craig and Antonelli

[57] ABSTRACT

First and second magnetic poles are provided, which have end surfaces brought close and in opposition to a material to be examined. These magnetic poles are magnetized by a DC exciter coil such that the magnetic poles have opposite polarities. The first magnetic pole is provided at its end surface with a pair of cumulatively connected transmitting coils, and the second magnetic pole is provided at its end surface with a pair of differentially connected receiving coils. The transmitting coils are connected to a pulser which generates a pulse current, and the receiving coils are connected to a differential amplifier. An electromagnetic ultrasonic wave generated by the transmitting coils are received by the receiving coils, amplified by the differential amplifier, and thereafter supplied to a synchroscope and an automatic detector.

7 Claims, 12 Drawing Figures

ELECTROMAGNETIC ULTRASONIC APPARATUS

BACKGROUND OF THE INVENTION

1. Field of the Invention

The present invention relates to an electromagnetic ultrasonic apparatus and, more particularly, to an electromagnetic ultrasonic apparatus which permits examining the quality of conductive materials, for example, metal strips, ingots and bullet type steel and aluminum without being brought into contact therewith.

2. Description of the Prior Art.

An electromagnetic ultrasonic apparatus permits transmitting and receiving ultrasonic waves as it is in a non-contact state, and is useful as an instrument for examining materials, without destroying the same, for example, moving materials, and materials which are difficult to physically contact due to the temperature or shape thereof.

An electromagnetic ultrasonic apparatus comprising a transmitting magnetic pole provided such that the front end surface of the transmitting magnetic pole can be brought close and in opposition to one surface of a material to be examined, a receiving magnetic pole which is provided such that the front end surface of the receiving magnetic pole can be brought close and in opposition to the opposite surface of the material and which has a magnetic polarity opposite to that of the transmitting magnetic pole, an exciter coil for supplying a DC magnetic field to the transmitting and receiving magnetic poles, and transmitting and receiving coils provided at the front end surfaces of the transmitting and receiving magnetic poles is described in, for example, "British Journal of NDT", July 1977, pages 178-184, G. J. Parkinson and D. M. Wilson.

In the above apparatus, a mode conversion echo occurring when ultrasonic waves are reflected within a material being examined is received as noise and cause the SN ratio to be decreased. Therefore, this apparatus is not sufficiently high in capability of detecting flaws in a material.

Japanese Patent Laid-open No. 86388/1977 shows that, when two electromagnetic ultrasonic apparatuses are arranged close to each other to utilize the difference between output voltages occurring in both of the receiving coils, the mode conversion echo and external noise are deadened with each other. In this apparatus, the difference between waves passed through a material being examined and back face echo can be obtained as an output from the receiving coils so that the capability of this apparatus of detecting flaws in a material is improved to a considerable, but not sufficient, extent.

SUMMARY OF THE INVENTION

Therefore, an object of the present invention is to provide an electromagnetic ultrasonic apparatus having a high capability of detecting flaws in a material.

The output voltages of receiving coils of an electromagnetic ultrasonic apparatus vary depending upon various electromagnetic conditions, for example, magnetic flux density B, air gap G between transmitting and receiving coils and the surfaces of a material being examined, and specific permeability $\mu s$ of the material. For example, when the gap G between transmitting and receiving coils and the surfaces of a material being examined is varied by 1 mm, the output voltages of the receiving coils are varied by approximately 6 dB. This is due to variation in the degree of magnetic combination of the transmitting and receiving coils and the surfaces of the material being examined, which is caused by variation in the width of the gap G. When the magnetic flux density is varied by 1%, the output voltages of the receiving coils are varied by approximately 5 dB. Therefore, in order to improve the capability of detecting flaws in a material of an electromagnetic ultrasonic apparatus, wherein a differential output of receiving coils is used, it is important that the electromagnetic conditions for two sets of transmitting and receiving coils be in agreement with each other.

According to the present invention, two sets of transmitting coils and receiving coils are provided at the front end surface of one transmitting magnetic pole and one receiving magnetic pole, respectively. This makes it possible to arrange the transmitting coils and receiving coils such that they are spaced from each other by not more than 1 cm. As a result, the electromagnetic conditions for two sets of transmitting coils and receiving coils resemble each other. This allows the flaw detecting capability of the electromagnetic ultrasonic apparatus to be improved.

To this end, the present invention provides an electromagnetic ultrasonic apparatus for examining materials by using ultrasonic waves, comprising a first magnetic pole having an end surface which is brought close and in opposition to a material to be examined; a second magnetic pole having an end surface which is brought close and in opposition to the material, and a polarity opposite to that of the first magnetic pole; a DC magnetic field generating means for supplying a DC magnetic field to the first and second magnetic poles; a pair of transmitting coils which are provided between the material and the end surface of the first magnetic pole and which face different portions of a surface of the material; a pair of receiving coils which are provided in either a space between the material and the end surface of the first magnetic pole or a space between the material and the end surface of the second magnetic pole and which are opposed to the transmitting coils, respectively; a pulse signal generating means for supplying a pulse current to the transmitting coils; and a signal control means for amplifying and controlling output signals generated in the receiving coils, the transmitting coils and receiving coils being connected together such that output signals generated in the receiving coils have differential relationship with each other.

The above and other objects as well as the advantageous features of the invention will become apparent from the follwing description of the preferred embodiment taken in conjunction with the accompanying drawings,

BRIEF DESCRIPTION OF THE DRAWINGS

FIGS. 6A-C shows the waveforms of outputs from some parts of the embodiment shown in FIG. 1, in a case where the material being examined has no flaws therein, wherein FIGS. 6A and 6B show the waveforms of outputs from receiving coils, and FIG. 6C shows the waveform of an output from a differential amplifier;

FIGS. 7A-C shows the waveforms of outputs from some parts of the embodiment shown in FIG. 1, in a case where the material being examined has a flaw, wherein FIGS. 7A and 7B show the waveforms of outputs from receiving coils, and FIG. 7C shows the waveform of an output from a differential amplifier.

DESCRIPTION OF THE PREFERRED EMBODIMENT

Figure 1:
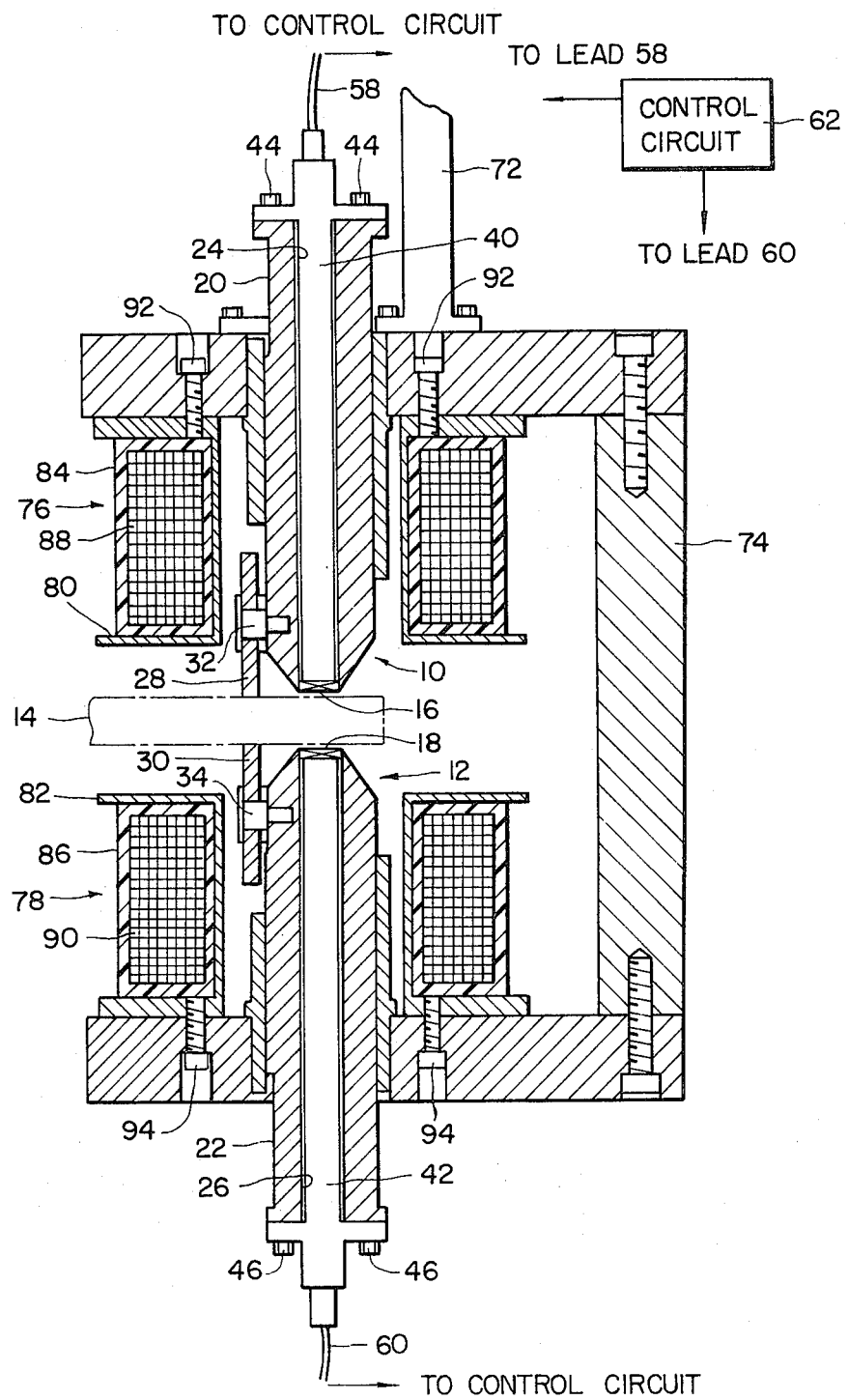
FIG. 1 is a sectional view of an electromagnetic ultrasonic apparatus embodying the present invention.
Figure 2:
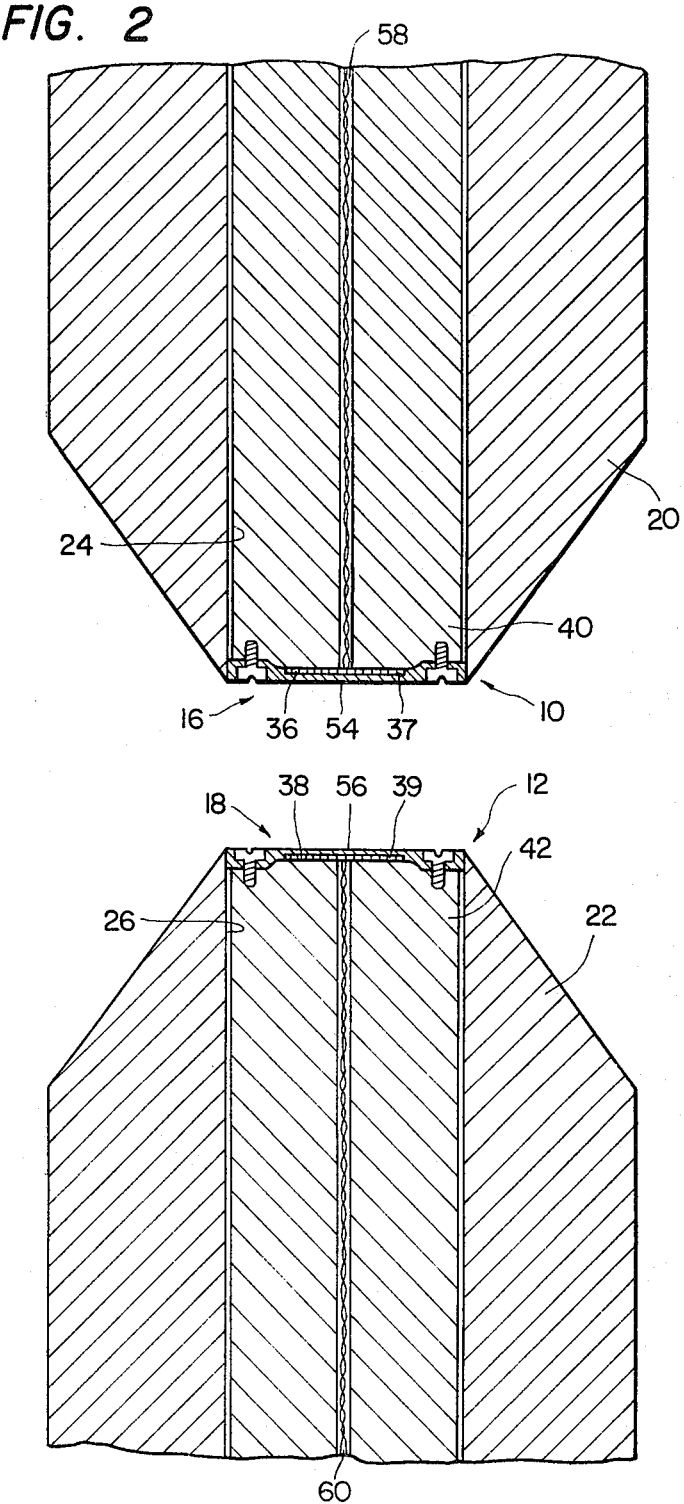
FIG. 2 is an enlarged sectional view of magnetic pole portions of the embodiment shown in FIG. 1.
Figure 3:
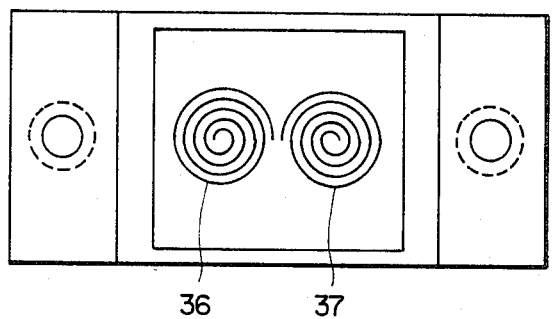
FIG. 3 is a plan view showing the arrangement of transmitting coils in the embodiment shown in FIG. 1.

Referring to FIGS. 1, 2 and 3, magnetic poles 10, 12 have end surfaces 16, 18, respectively, which are close and in opposition to a conductive material 14 to be examined. The material 14 consists of, for example, a hot strip being subjected to a rolling step. Magnetic members 20, 22, which constitute the magnetic poles 10, 12, respectively, have cassette holding bores 24, 26 in the central portions thereof, and are kept spaced from the material 14 by a predetermined distance by means of rolls 28, 30 which are in contact with the material 14. The rolls 28, 30 are rotatably supported on the side surfaces of the magnetic members 20, 22 via shafts 32, 34.

Cassettes 40, 42, to the ends of which transmitting coils 36, 37, and receiving coils 38, 39 are attached (see FIG. 2), respectively, are inserted into the cassette holding bores 24, 26 to be secured to the members 20, 22 with screws 44, 46. The cassette 40 is provided on its lower end surface with a ceramic coil retainer 54 having a thermal resistance, and the transmitting coils 36, 37 are formed at the inner side of the coil retainer 54 by a printing wiring technique.

The transmitting coils 36, 37 are provided close to each other in the same plane which is in the magnetic field of the magnetic pole 10 and which is parallel to the end surface 16 thereof, and cumulatively connected to each other.

The cassette 42 is provided on its upper end surface with a material having a thermal resistance, for example, a ceramic coil retainer 56, and the receiving coils 38, 39 are formed at the inner side of the coil retainer 56 by a printing wiring technique. The receiving coils 38, 39 are provided close to each other in the same plane which is in the magnetic field of the magnetic pole 12 and which is parallel to the end surface 18 thereof, and differentially connected to each other.

The transmitting and receiving coils 36, 37, 38, 39 are formed to selected dimensions; they have, for example, an outer diameter of 10 mm, an inner diameter of 0.8 mm and 15 turns of winding. These transmitting and receiving coils 36, 37; 38, 39 are provided in alignment and close to each other on the end surfaces 16, 18 of the magnetic poles 10, 12 such that the distance between the center of coils is approximately 10 mm. Since the end surfaces 16, 18 of the magnetic poles 10, 12 are kept spaced by a predetermined distance from the material to be examined, by means of the rollers 28, 30, the distance between the transmitting coils 36, 37 and the material 14 and the distance between the receiving coils 38, 39 and the material 14 are kept at a predetermined level, for example, 1.7 mm. The transmitting and receiving coils 36, 37; 38, 39 are connected to a control circuit 62 via lead wires 58, 60, respectively. The transmitting and receiving coils can be withdrawn with the cassettes 40, 42 from the magnetic members 20, 22 after the screws 44, 46 have been removed.

The magnetic poles 10, 12 are fixed to a frame 74 which is secured to a support 72. DC magnetic field generating means 76, 78 surrounding the magnetic poles 10, 12 consist of coil bobbins 80, 82, insulating materials 84, 86, and DC exciter coils 88, 90. The coil bobbins 80, 82 are fastened to the frame 74 with screws 92, 94. The DC exciter coils 88, 90 are connected to a DC power source and generate in the magnetic poles 10, 12 magnetic fields which cause the magnetic flux densities to be 2 teslas.

Figure 4:
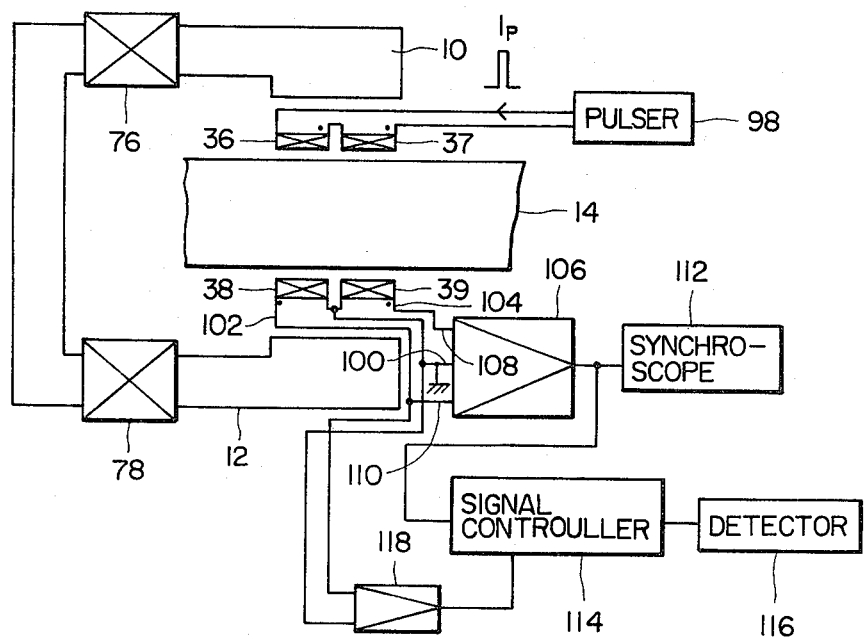
FIG. 4 is a block diagram of a control circuit in the embodiment shown in FIG. 1.

The transmitting coils 36, 37 are connected to a pulser 98 as shown in FIG. 4, which generates a pulser current Ip. The receiving coils 38, 39 are differentially connected to each other, and a node 100 thereof is grounded. The remaining output terminals 102, 104 are connected to input terminals 108, 110 of a differential amplifier 106. An output from the differential amplifier 106 is supplied to an observation unit, for example, a synchroscope 112 so as to be displayed in image. An output from the differential amplifier 106 is also supplied to a signal controller 114 to be input into an automatic detector 116. A gate amplifier 118 causes the output from the signal controller 114 to be supplied to the automatic detector 116 for a predetermined period of time, and actuate the detector 116 when the output from the signal controller 114 has exceeded a predetermined level.

When a pulse current Ip is supplied from the pulser 98 to the transmitting coils 36, 37, eddy currents occur at the upper and lower surfaces of the material 14 due to high frequency magnetic field generated by the pulse current. The eddy currents and DC magnetic field act on each other to generate stress waves (ultrasonic waves) in accordance with Fleming's left-hand rule. The stress waves are propagated as oscillatory waves in the direction of the thickness of the material being examined, to reach the bottom surface thereof. The waves which have reached the bottom surface of the material generate a high frequency magnetic field by an electromagnetic process opposite to the electromagnetic process by which the stress waves are generated. Namely, the oscillatory stress waves and DC magnetic field act on each other at the bottom surface of the material, and an electric current in accordance with Fleming's right-hand rule flows to the lower surface of the material. Due to the magnetic field generated by this electric current, a voltage occurs in the receiving coils 38, 39.

The principle of generation of the above-described electromagnetic ultrasonic waves is explained in detail in "British Journal of NDT", G. J. Parkinson and D. M. Wilson, pages 178-184, July 1977.

When the material being examined has no flaws, the electromagnetic waves (transversal waves) generated by the transmitting coils 36, 37 directly reach the receiving coils 38, 39. Since reception outputs generated in the receiving coils 38, 39 are of substantially the same amplitude and waveform, a differential output (an output from the differential amplifier 106) is substantially zero.

Figure 5:
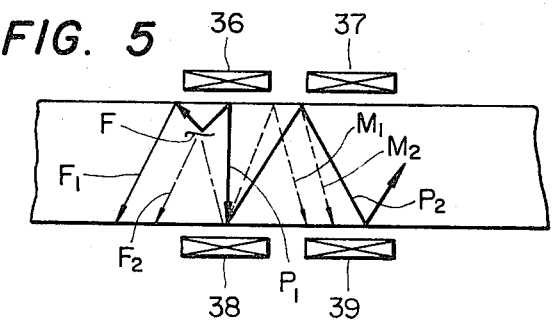
FIG. 5 is a sectional view showing an electromagnetic ultrasonic wave advancing in a material being examined.
Figure 6A:
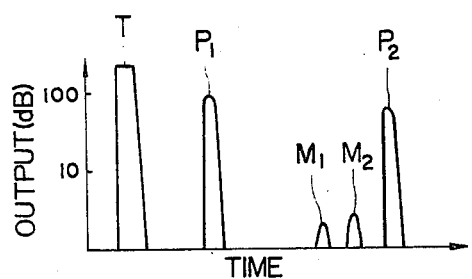
Figure 6B:
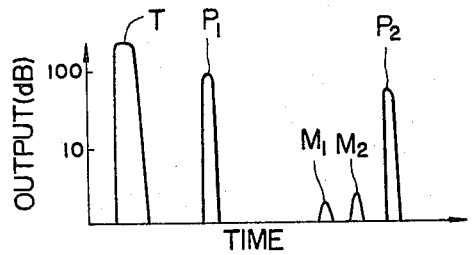

The above embodiment will be described in more detail with reference to FIGS. 5 and 6.

Figure 7A:
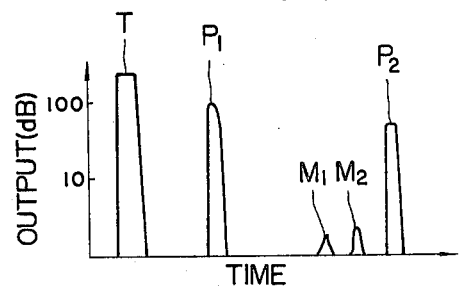
Figure 7B:
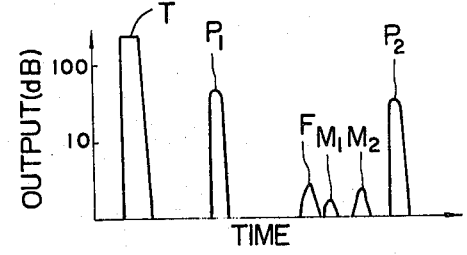
Figure 6C:
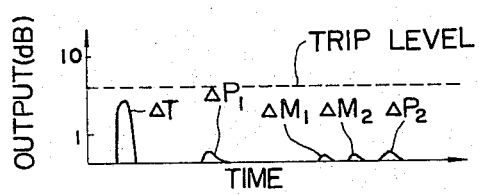
Figure 7C:
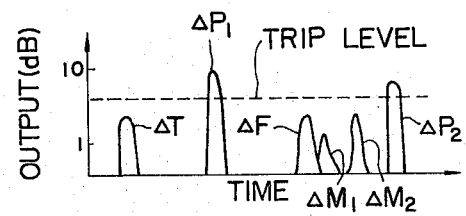

When a sending pulse T is supplied to the pulser 98, a first transmitted wave $P_1$ is received by the receiving coils 38, 39. When the first transmitted wave $P_1$ is reflected on the bottom surface of the material, a mode conversion echo $M_1$ (longitudinal wave) is generated. When the first transmitted wave $P_1$ reflected on the bottom surface of the material is then reflected on the upper surface thereof, a mode conversion echo $M_2$ (longitudinal wave) is generated. Since the mode conversion echoes $M_1$, $M_2$ advance at a high speed, they are received by the receiving coils 36, 37 at times shown in FIGS. 6A and 6B. After the mode conversion echoes $M_1$, $M_2$ have been received by the receiving coils 36, 37, a second transmitted wave $P_2$ is received thereby. Accordingly, an output from the differential amplifier 106 is as shown in FIG. 6C. The transmitting coils 36, 37 and receiving coils 38, 39 in this embodiment are provided close to each other on the same end surfaces 16, 18 of the magnetic poles 10, 12, respectively, so that gaps between the transmitting and receiving coils 36, 37; 38, 39 and the material 14 are kept substantially the same. Also, when the material 14 has no flaws, an output from the differential amplifier 106, i.e. noises are kept low. When the material has a flaw F just above the receiving coil 38 as shown in FIG. 5, it causes flaw waves $F_1$, $F_2$ to occur. It also causes the amplitudes of the first transmitted wave $P_1$, second transmitted wave $P_2$, and mode conversion echoes $M_1$, $M_2$ to be decreased to a small extent. As a result, outputs from the receiving coils 38, 39, and differential amplifier 106 are as shown in FIGS. 7A, 7B and 7C. The waveform of an output supplied from the differential amplifier 106 into the synchroscope 112 is identical with those shown in FIGS. 6C and 7C. Therefore, when the detection level is, for example, 6 dB, the output illustrated in FIG. 6C from the differential amplifier 106 is judged that the material has no flaws, and the output illustrated in FIG. 7C from the differential amplifier 106 is judged that the material has a flaw.

The signal control circuit 114 is adapted to set a gate width and a threshold level in accordance with the purpose of measurement to actuate the automatic detector 116. A gate amplifier 118 causes an output from the signal control circuit 114 to be input into the detector 116 for only such a period of time that a first transmitted wave $P_1$ is generated. (The length of the time is set in accordance with the thickness of the material to be examined.) Therefore, the first transmitted wave $P_1$ only is input into the detector 116. When such an input into the detector 116 has exceeded a threshold level, for example, 6 dB, an output is generated therein to indicate the existence of a flaw in the material or give warning.

Figure 8:
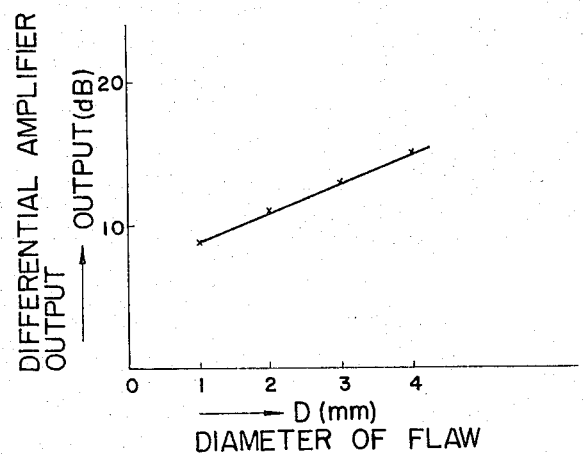
FIG. 8 is a graphical diagram showing an example of flaw detection characteristics of the embodiment shown in FIG. 1.

FIG. 8 is a graphical diagram showing the flaw detection characteristics of the above-described embodiment, wherein the gap between the end surfaces of the magnetic poles and a material to be examined, and the magnetic flux density are set to 1.7 mm and 2 teslas, respectively. According to this embodiment, a flaw of 1 mm in diameter could be detected at a SN ratio of approximately 9 dB.

The present invention is not, of course, limited to the above embodiment; it may be modified in various ways within the scope of the appended claims.

We claim:

1. An electromagnetic ultrasonic apparatus for examining materials by using ultrasonic waves, comprising a first magnetic pole having a continuous end surface which is in close proximity and in opposition to a material to be examined; a second magnetic pole having a continuous end surface which is in close proximity and in opposition to the material, and having a polarity opposite to that of said first magnetic pole; DC magnetic field generating means for supplying a DC magnetic field to said first and second magnetic poles; a pair of transmitting coils which are provided between the material and the end surface of said first magnetic pole and which face different portions of a surface of the material; a pair of receiving coils which are provided in a space between the material and the end surface of said second magnetic pole and which are opposed to said transmitting coils, respectively; pulse signal generating means for supplying a pulse current to said transmitting coils; and signal control means for amplifying and controlling output signals generated in said receiving coils, said transmitting coils and said receiving coils being connected together such that output signals generated in said receiving coils have differential relationship with each other.

2. An electromagnetic ultrasonic apparatus according to claim 1, wherein said DC magnetic field generating means consist of DC exciter coils wound around said first and second magnetic poles.

3. An electromagnetic ultrasonic apparatus according to claim 1, wherein said transmitting coils and said receiving coils are supported on cassettes which are inserted into the central portion of said first and second magnetic poles, respectively, so as to be detachably fixed therein.

4. An electromagnetic ultrasonic apparatus according to claim 1, wherein said first and second magnetic poles are provided with means including rollers which roll on the surfaces of a material to be examined for maintaining gaps between the end surfaces of said first and second magnetic poles and those of the material to be examined.

5. An electromagnetic ultrasonic apparatus for examining materials by using ultrasonic waves, comprising a first magnetic pole having a continuous end surface which is brought into close proximity and in opposite to a material to be examined; a second magnetic pole having a continuous end surface which is brought into close proximity and in opposition to the material, and having a polarity opposite to that of said first magnetic pole; DC magnetic field generating means for supplying a DC magnetic field to said first and second magnetic poles; a pair of transmitting coils provided between the material and the continuous end surface of said first magnetic pole, cumulatively connected with each other, and facing different portions of a surface of the material; a pair of receiving coils provided in a gap between the material and the continuous end surface of said second magnetic pole, differentially connected with each other, and opposed to said transmitting coils; pulse signal generating means for supplying a pulse current to said transmitting coils; and signal control means for amplifying and controlling output signals generated in said receiving coils.

6. An electromagnetic ultrasonic apparatus for examining materials by using ultrasonic waves, comprising a first magnetic pole having a continuous end surface which is brought into close proximity with and in opposition to a material to be examined; a second magnetic pole having an end surface which is brought into close proximity with and in opposition to the material, and having a polarity opposite to that of said first magnetic pole; DC magnetic field generating means for supplying a DC magnetic field to said first and second magnetic poles; a pair of transmitting coils which are provided in alignment with each other between the material and the end surface of said first magnetic pole and in a plane parallel to the continuous end surface of said first magnetic pole and which are cumulatively connected with each other; a pair of receiving coils which are provided in alignment with each other between the material and the continuous end surface of said second magnetic pole and in a plane parallel to the end surface of said second magnetic pole and which are differentially connected with each other; pulse signal generating means for supplying a pulse current to said transmitting coils; amplifier means for amplifying output signals generated in said receiving coils; and means actuated in response to signals relating to either transmitted waves or bottom echoes at the output from said amplifier means for indicating a flaw in said material.

7. An electromagnetic ultrasonic apparatus for examining materials by using ultrasonic waves comprising:

a first magnetic pole having a continuous end surface which is brought into close proximity and in opposition to the materials to be examined;

a second magnetic pole having a continuous end surface which is brought into close proximity and in opposition to the materials and having a polarity opposite to that of said first magnetic pole;

a DC magnetic field generating means for supplying said first and second magnetic poles with a DC magnetic field;

a transmitting coil provided on the end surface of one of said first and second magnetic poles;

a receiving coil provided on the end surface of the other of said first and second magnetic poles;

pulse signal generating means for supplying said transmitting coil with a pulse current;

signal control means for amplifying and controlling output signals generated in said receiving coil, at least one of said transmitting and receiving coils including a pair of partial coils and being disposed on the same end surface, and being connected together such that output signals generated in the partial coils of said receiving coil have a differential relationship with each other.

* * * * *